(12) United States Patent
Gaillot et al.

(10) Patent No.: US 11,577,027 B2
(45) Date of Patent: Feb. 14, 2023

(54) PLUNGER AND METHOD OF MANUFACTURING A PLUNGER

(71) Applicant: HOFFMANN-LA ROCHE INC., Little Falls, NJ (US)

(72) Inventors: Maxime Gaillot, Basel (CH); Alan Dwyer, Clinton, MA (US); Pascal Launois, Clinton, MA (US); Julian McDonnell, Clinton, MA (US); Eoin Connaughton, Clinton, MA (US); Mark Digby Teucher, Bristol (GB); Jonathan Paul Ridley, Bristol (GB)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 17/258,899

(22) PCT Filed: Jul. 9, 2019

(86) PCT No.: PCT/EP2019/068349
§ 371 (c)(1),
(2) Date: Jan. 8, 2021

(87) PCT Pub. No.: WO2020/011762
PCT Pub. Date: Jan. 16, 2020

(65) Prior Publication Data
US 2021/0290852 A1 Sep. 23, 2021

(30) Foreign Application Priority Data
Jul. 10, 2018 (EP) .................................... 18182615

(51) Int. Cl.
*A61M 5/315* (2006.01)

(52) U.S. Cl.
CPC .... *A61M 5/31511* (2013.01); *A61M 5/31513* (2013.01); *A61M 5/31515* (2013.01); *A61M 2207/00* (2013.01)

(58) Field of Classification Search
CPC ................................................. A61M 5/31515
See application file for complete search history.

(56) References Cited

U.S. PATENT DOCUMENTS

| 6,190,363 B1 | 2/2001 | Gabbard et al. |
| 2005/0015057 A1 | 1/2005 | Steenfeldt-Jensen et al. |

(Continued)

FOREIGN PATENT DOCUMENTS

| CN | 201643230 U | 11/2010 |
| CN | 102772843 A | 11/2012 |

(Continued)

OTHER PUBLICATIONS

International Search Report dated Sep. 10, 2019 in Intl. Appl. No. PCT/EP2019/068349.

(Continued)

*Primary Examiner* — Dung T Ulsh
(74) *Attorney, Agent, or Firm* — Medler Ferro Woodhouse & Mills PLLC (57) ABSTRACT

A plunger (1) for a medical delivery device comprises: a rod element (2) having a distal end (22) and a proximal end, and a stopper (3) mounted to the rod element (2) at its distal end (22). The rod element (2) has a first form fit structure (24) and the stopper (3) has a second form fit structure (31). The stopper (3) is locked to the rod element (2) by the first form fit structure (24) of the rod element (2) and the second form fit structure (31) of the stopper (3) engaging each other.

14 Claims, 3 Drawing Sheets

(56) References Cited

U.S. PATENT DOCUMENTS

| | | |
|---|---|---|
| 2011/0028913 A1 | 2/2011 | Muramatsu et al. |
| 2011/0034882 A1* | 2/2011 | Quinn ................ A61M 5/31511 |
| | | 604/218 |
| 2012/0253291 A1* | 10/2012 | Ivosevic ........... A61M 5/31515 |
| | | 604/222 |
| 2012/0289899 A1 | 11/2012 | Wu |
| 2014/0116246 A1 | 5/2014 | Melander |
| 2015/0209521 A1 | 7/2015 | Titus et al. |
| 2017/0203046 A1* | 7/2017 | LaRose ................ A61L 31/048 |

FOREIGN PATENT DOCUMENTS

| | | |
|---|---|---|
| CN | 105939744 A | 9/2016 |
| DE | 21 47 823 A1 | 3/1973 |
| JP | H01172843 U | 12/1989 |
| JP | H05317424 A | 12/1993 |
| JP | 2007125130 A | 5/2007 |
| JP | 2012135664 A | 7/2012 |
| WO | 01/97885 A1 | 12/2001 |

OTHER PUBLICATIONS

Chinese Office Action dated Jul. 5, 2022, in Chinese Patent Appl. No. 201980046031.1 (with English translation).

* cited by examiner

PLUNGER AND METHOD OF MANUFACTURING A PLUNGER

TECHNICAL FIELD

The present invention relates to a plunger according to the preamble of independent claim 1 and more particularly to a method of manufacturing a plunger. Such plungers having a rod element with a distal end and a proximal end as well as a stopper mounted to the rod element at its distal end, can be used in various different medical delivery devices such as syringes, autoinjectors, dosing devices, combined dosing and (auto-)injection apparatus, and the like.

BACKGROUND ART

Delivering a liquid or other fluid out of a container is required in many medical or pharmaceutical applications and performed in a plurality of different ways. Particularly where it is essential that the liquid is comparably precisely provided, specific devices are commonly used. For example, liquid pharmaceutical substances are often provided in glass or plastic vials which are closed by a septum or rubber plug and a cap clamped around it or another similar seal cover. Conventionally, for delivering the pharmaceutical substance out of vials, syringes are used. Thereby, a needle of the syringe penetrates the septum or cover and the pharmaceutical substance is withdrawn into the syringe through its needle. Once transferred into the syringe, the pharmaceutical substance is delivered in an appropriate manner. For example, the pharmaceutical substance can be, e.g. subcutaneously or intramuscularly, injected or it can be orally applied or provided as droplets, e.g., in the eyes or nose of the patient.

Delivering liquids from vials or containers by means of syringes usually is comparably difficult. It is typically necessary that an educated person such as a doctor or a nurse is involved. In particular, in cases where the dosage of liquid delivered has to be comparably precise such as when comparable small volumes as in a range of ten microliter to about one milliliter are involved patients are typically not capable of performing the delivery themselves when using a syringe or a similar device. This is, self-administration can be challenging for the user. However, self-administration of liquids or medicaments is beneficial in many therapeutic applications since the effort for the patient and the costs of the therapy can be extensively reduced.

For improving this situation, there are devices used which allow for more conveniently delivering a comparably precise volume of liquids. For example, it is known to provide medicaments in prefilled syringes which can be administered by the patients themselves. However, such prefilled syringes are often not preferred for plural reasons. For example, producing prefilled syringes is comparably complicated and expensive compared to vials in terms of manufacturing. Or, syringes have to be provided with plural possible dosages suitable for different applications and patients, which makes manufacture comparably cumbersome. Other examples of delivery devices are injection pens which are often used in therapy of diabetes.

A further medical delivery device is described in WO 2017/102742 A1 which is designed for automatically injecting a predefined dosage of a liquid into a patient. The device has a vial seat and a dosing mechanism with a dosing member and a rod element for defining an amount of liquid to be delivered before administration. The rod element or plunger has a stem and a stopper located at a distal end of the stem. The dosing member has a chamber body and a needle connected to the chamber body. By rotating the rod element and dosage member relative to each other about a longitudinal axis the rod member is translationally moved relative to the chamber body. Thereby, a dosage chamber is created between the needle and the stopper in the chamber body of the dosage member. The needle is connected to the vial positioned in the seat such that liquid is withdrawn from the vial via the needle into the dosage chamber. Thus, by said rotation the amount of liquid to be dosed can be adjusted by a user of the device.

In known medical delivery devices the plungers typically include a rod and a stopper located at a distal end of the rod. Thereby, the stoppers are often connected or attached to the rods such that the complete plunger can be operated as one unit. For example, it is known to connect the stopper to the rod by using an adhesive, by snapping the stopper on the rod, by screwing the rod into the stopper, and the like. Since the stopper has to tightly fit into a chamber containing a liquid to be delivered, it has on one hand to be elastic to a certain extent. For that purpose, the stopper preferably is soft and flexible such that it can be pressed and deformed to the chamber wall. In particular, the more flexible the stopper is the better the chamber can be tightly closed by the stopper.

On the other hand, when moving the stopper relative to the chamber, friction and pressure forces act on the stopper which may deform the stopper such that tightness and dosing accuracy may be impaired. When the plunger is used for withdrawing the liquid into the chamber, these forces may in addition tear the stopper from the rod such that proper plunger function can no longer be guaranteed. Furthermore, as described above, in addition to a translational movement a rotational movement between stopper and chamber can be involved which additionally stresses or deforms the stopper. Thus, to minimize such impairments the stopper should be comparable strong or stiff such that it can be well connected to the rod. These needs to the properties of the stopper may contradict the needs for its tightness such that typically a compromise is made which has drawbacks in either of the properties required.

Therefore, there is a need for a plunger having a stopper connected to a rod element which allows for providing sufficient tightness when being arranged in a chamber as well as sufficient dosing accuracy when being used.

DISCLOSURE OF THE INVENTION

According to the invention this need is settled by a plunger as it is defined by the features of independent claim 1 and by a method as it is defined by the features of independent claim 14. Preferred embodiments are subject of the dependent claims.

In one aspect, the invention is a plunger for a medical delivery device comprising a rod element having a distal end and a proximal end, and a stopper mounted to the rod element at its distal end. The rod element has a first form fit structure and the stopper has a second form fit structure. The stopper is locked to the rod element by the first form fit structure of the rod element and the second form fit structure of the stopper inter-engaging.

The medical delivery device can be an apparatus configured to deliver a typically liquid drug substance in an appropriate form. Particularly, it can be an injection apparatus such as a syringe, an autoinjector for applying a drug substance, a dosing device, or a combined dosing and (auto-)injection apparatus.

The term "distal end" in connection with the rod element relates to a side of the rod element which is directed towards a substance when advancing the plunger for delivering the substance. In particular, when being implemented in the medical delivery device, the plunger typically is translationally moved for pressing the typically liquid substance out of the device. Often the medical delivery device is equipped with a needle and the substance is delivered through the needle into a patient by injection. Analogously, the term "proximal end" relates to a side of the rod element which is directed away from the distal end. Thus, typically the distal and proximal ends are opposite to each other.

The term "drug" as used herein relates to a therapeutically active agent, also commonly called active pharmaceutical ingredient (API), as well as to a combination of plural such therapeutically active substances. The term also encompasses diagnostic or imaging agents, like for example contrast agents (e.g. MRI contrast agents), tracers (e.g. PET tracers) and hormones, that need to be administered in liquid form to the patient.

The term "drug substance" as used herein relates to a drug as defined above formulated or reconstituted in a form that is suitable for administration to the patient. For example, besides the drug, a drug substance may additionally comprise an excipient and/or other auxiliary ingredients. A particularly preferred drug substance in the context of the invention is a drug solution, in particular a solution for oral administration, injection or infusion.

The term "drug product" as used herein relates to a finished end product comprising a drug substance or a plurality of drug substances. In particular, a drug product may be a ready to use product having the drug substance in an appropriate dosage and/or in an appropriate form for administration. For example, a medical delivery device, an injection apparatus or a prefilled syringe may be a drug product.

The term "inter-engage" as used in connection with the first and second form fit structures relates to these structures engaging each other. Thereby, elements of the one structure can arranged in elements or portions of the other structure.

The term "form fit" as used herein generally relates to a connection between two parts interlocking. In particular, for interlocking an element of the one part is in the way of an element of the other part such that these elements cannot pass each other. In connection with the rod element and the stopper, when being locked, the first and second form fit structures are in the way of each other, particularly along an axis of the plunger, such that they inter-engage.

Thereby, the form fit structures can be equipped with mating male and female portions located inside each other for engaging. As described in more detail below for preferred embodiments, the first and second form fit structures can have one or more protrusions or projections and corresponding recesses. When engaging, the protrusions or projections are located inside the recesses.

By equipping the rod element and the stopper with the first and second form fit structures, the stopper can be securely fixed to the rod element such that the complete plunger is one unit. In particular, these structures allow for providing a tight fit or form fit connection which is sufficiently strong to resist forces induced in operation of the plunger within a medical deliver device without substantially deforming the stopper. Thereby, the form fit connection can suffice already for being secure or it can be additionally supported by friction fit or the like. However, the form fit connection allows for providing a connection between the rod element and the stopper which is essentially stronger than pure friction fitting and essentially simpler to construct than by using an adhesive. This allows for using a comparably flexible material for manufacturing the stopper and nevertheless to provide sufficient resistance to the forces involved in use.

As mentioned above, the first and second form fit structures can be equipped with male and female portions. Thereby, preferably the first form fit structure of the rod element is a cavity structure and the second form fit structure of the stopper is a projection structure, and the stopper is locked to the rod element by the projection structure of the stopper being arranged in the cavity structure of the rod element. Thus, the first form fit structure of the stopper and the second form fit structure of the rod element engage by the projection structure of the stopper being arranged in the cavity structure of the rod element.

The term "cavity structure" as used in connection with the rod element can relate to one or plural indentations, pits, recesses, depressions, channels, chambers, any combination thereof or the like. Similarly, the term "projection structure" as used in connection with the stopper can relate to one or plural protuberances, bulges, bars, any combination thereof or the like, which correspond to the cavity structure.

Preferably, the rod element is made of a rod material and the stopper is made of a stopper material, the rod material being more rigid and less elastic than the stopper material. For example, the rod material can be an acrylonitrile butadiene styrene (ABS) which is a comparably rigid plastic material. The stopper material can be a thermoplastic elastomer (TPE) which is a comparably soft and elastic plastic material. By having such different materials used in the rod element and the stopper, an advantageous configuration of the plunger can be achieved which allows for a proper application and tightness in the medical delivery device.

Preferably, the second form fit structure of the stopper has an anchor portion with a preferably axially extending shaft section and an arm section, and the first form fit structure of the rod element has an arm socket, the arm section of the second form fit structure of the stopper radially projecting from the shaft section of the second form fit structure of the stopper, the arm socket of the first form fit structure of the rod element correspondingly radially oriented, and the arm section of the second form fit structure of the stopper being arranged inside the arm socket of the first form fit structure of the rod element.

The terms "axially", "axis" and similar as used herein relate to an axis of the plunger which longitudinally extends through the distal and proximal ends of the rod element. The axis can define a direction into which the plunger is moved for delivering or withdrawing a drug substance out of or into, respectively, the delivery device. In particular, the axis can be centrally in the plunger extending through the complete rod element and stopper. The term "radial" as used herein can relate to a direction perpendicular or otherwise angled to the axis. Thus radially projecting can relate to extending in an angle and particularly in a right angle away from the axis.

The anchor portion of the stopper and corresponding structure in the rod element allows for providing a comparably large form fit force and for reducing possible stopper deformation. Like this, it allows for connecting the stopper to the rod element in a manner that it cannot be removed without impairing or destroying the plunger. Particularly, the arm section of the anchor portion radially extending and received by the corresponding arm socket allows for blocking essentially any axial movement and deformation of the stopper relative to the rod element.

In an advantageous embodiment the anchor portion of the stopper has one or more arm sections and the rod element correspondingly one or more arm sockets. For example, there can be two arm sections and arm sockets provided. The arm section(s) and the arm socket(s) may radially taper towards the axis of the plunger. In other words, the dimension of the arm section(s) and the arm socket(s) may increase in a radial direction starting from the axis. Like this, any radial movement of the arm section(s) can be blocked.

The shaft section of the anchor portion of the second form fit structure of the stopper can be centrally located in the stopper. It can extend along the axis of the stopper or plunger. Preferably, it comprises at least one lateral stabilization element configured to prevent or reduce deformation of the shaft section of the anchor portion of the second form fit structure of the stopper. The stabilization element(s) can particularly prevent a radial deformation as well as an axial deformation of the shaft section.

Thereby, the lateral stabilization element of the shaft section of the anchor portion of the second form fit structure of the stopper preferably has a wall section tapering along an axial direction towards a proximal end of the stopper. The proximal end of the stopper can be formed by the arm section of the anchor portion. Advantageously, the anchor portion is equipped with plural of such wall sections. The wall section(s) allow for efficiently providing stabilization of the stopper with regard to axial and radial deformations. Also, an anchor portion with such wall section(s) can be manufactured in a comparably efficient way.

The rod element preferably comprises a recess, in which the shaft section of the anchor portion of the second form fit structure of the stopper is arranged. Such recess can particularly be centrally extending along the axis of the plunger. In embodiments where shaft section has a tapering wall section, the recess can correspondingly be shaped in a cone like form.

Preferably, the stopper comprises a ring portion defining an inner radial stopper surface and an outer radial stopper surface, the rod element has a ring receiving section with an outer radial rod surface corresponding to the inner radial stopper surface of the stopper, the second form fit structure of the stopper has a circumferential protrusion radially extending from the inner radial stopper surface of the ring portion of the stopper, the first form fit structure of the rod element has a circumferential groove radially extending into the outer radial rod surface of the ring receiving section of the rod element, and the circumferential protrusion of the second form fit structure of the stopper is arranged in the circumferential groove of the first form fit structure of the rod element.

The term "circumferential" as used in connection with the protrusion and the groove can relate to an arrangement about the axis of the plunger and along the inner or outer surface. Thereby, this term is not limited to arrangements extending along the complete circumference but also includes, for example, embodiments which are interrupted. However, advantageously the protrusion and groove both extend all about the axis, i.e. along the complete circumference.

Together with a distal end side of the stopper the ring portion can form a sleeve like cap which is imposed on the ring receiving section of the rod element. Like this, the stopper can encapsulate the distal end of the rod element. Thereby, the inner radial stopper surface is adjacent to and rests against the outer radial rod surface. By means of the circumferential protrusion and groove the stopper can be form fitted on the rod element particularly preventing an axial movement.

Thereby, the ring portion of the stopper preferably is equipped with a circumferential bulge radially extending from the outer radial stopper surface and radially aligned relative to the circumferential protrusion of the second form fit structure of the stopper. The bulge can, thus, extend normal to the axis of the device. It can be used for providing tightness between the stopper a chamber of the medical delivery device in which the plunger is arranged. In particular, the bulge can be pressed against a wall of the chamber thereby being slightly deformed to ensure tightness. Since, the bulge is radially aligned to the protrusion, i.e. it lies essentially in line with the protrusion, a comparably large amount of elastic material can be available for compression of the bulge. Specifically, the material of the bulge itself, of the ring portion as well as of the protrusion are available for being compressed when the stopper is inside the chamber of the medical delivery device. Like this, sufficient elasticity can be provided such that the stopper can be tightly fitted into the chamber.

Preferably, the second form fit structure of the stopper has a second circumferential protrusion radially extending from the inner radial stopper surface of the ring portion of the stopper, the first form fit structure of the rod element has a second circumferential groove radially extending into the outer radial rod surface of the ring receiving section of the rod element, and the second circumferential protrusion of the second form fit structure of the stopper is arranged in the second circumferential groove of the first form fit structure of the rod element.

The circumferential protrusion and the second circumferential protrusion can particularly be axially spaced from each other. Similarly, also the circumferential groove and the second circumferential groove can correspondingly be axially spaced from each other. Such second protrusion and groove allows for additionally form fitting or double form fitting the stopper to the rod element. Like this, the stopper can be additionally secured on the rod element.

Thereby, the ring portion of the stopper preferably is equipped with a second circumferential bulge radially extending from the outer radial stopper surface and radially aligned relative to the second circumferential protrusion of the second form fit structure of the stopper. Such second bulge can provide for tightness in addition to the first bulge mentioned above. Furthermore, it allows for ensuring or keeping a straight alignment of the stopper and particularly its outer surface when the stopper is moved within the chamber of the medical delivery device. This can assist in stabilizing the stopper on the rod element and in preventing deformation of the stopper.

Preferably, the stopper has a conical distal end portion, which can end in a tip. When being equipped with a ring portion, the ring portion can project from the distal end portion. Such conical end portion allows for efficiently pressing the liquid and for receiving the involved pressure with minimal deformation.

In another aspect, the invention is a method of manufacturing a plunger as described above. The method comprises obtaining a rod element of the plunger having a distal end, a proximal end and a first form fit structure. It further comprises molding a stopper of the plunger over the distal end of the rod element such that the stopper is equipped with a second form fit structure and that the stopper is locked to the rod element by the second form fit structure of the stopper and the first form fit structure of the rod element inter-engaging.

By such over-molding process for manufacturing the stopper, all elements or features of the stopper can efficiently be generated. Like this, the effects and benefits described above in connection with the plunger according to the invention and its preferred embodiments can efficiently and accurately be implemented.

BRIEF DESCRIPTION OF THE DRAWINGS

The plunger according to the invention and the method of manufacturing it are described in more detail herein below by way of exemplary embodiments and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
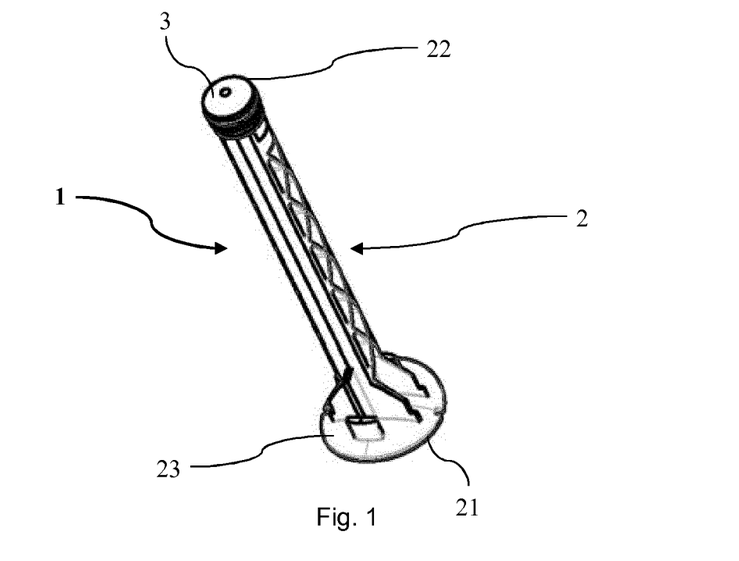
FIG. 1 shows a perspective view of a first embodiment of a plunger according to the invention.

FIG. 1 shows a perspective top view of a first embodiment of a plunger 1 according to the invention. The plunger 1 comprises a rod 2 as rod element and a stopper 3. The rod 2 is essentially stem like shaped, has a bottom proximal end 21 and a top distal end 22. At the proximal end 21 the rod 2 is equipped with a push plate 23 for receiving a force in order to forward the rod 2 in use. The stopper 3 is mounted to the rod 2 at its distal end 22.

Figure 2:
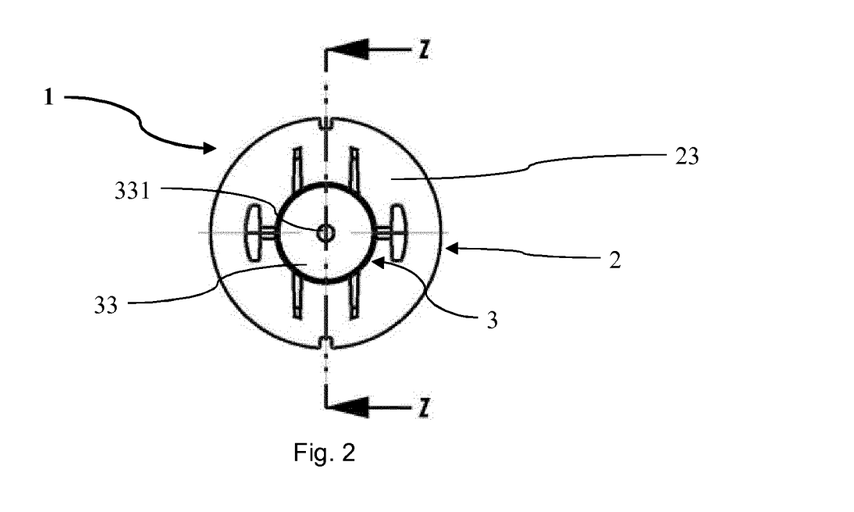
FIG. 2 shows top view on the plunger of FIG. 1.

In FIG. 2 the plunger 1 is depicted top down such that a distal end side portion 33 of the stopper 3 is faced. Centrally, the distal end side portion 33 has a tip 331. The stopper 3 as well as the push plate 23 have a circular outer circumference.

Figure 3:
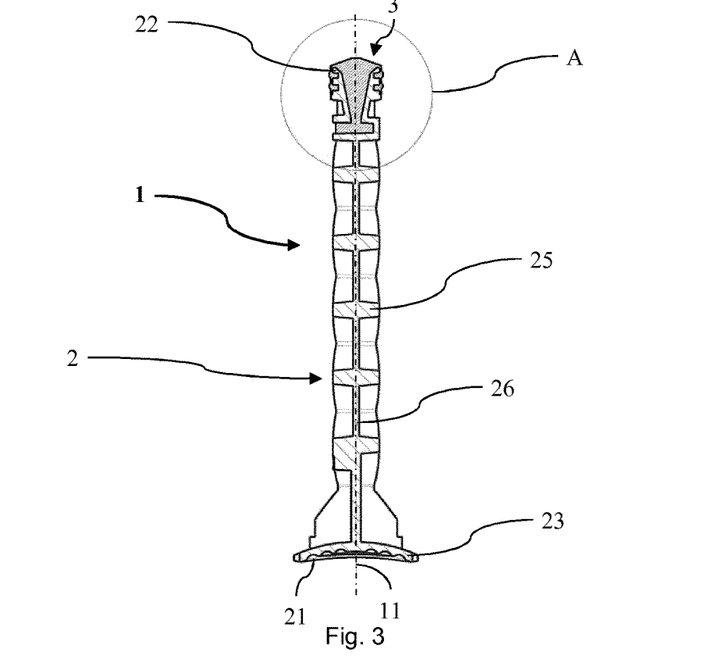
FIG. 3 shows a cross-sectional view along the line Z-Z of FIG. 2.

FIG. 3 shows a cross sectional view of the plunger 1. Thereby, an axis 11 of the plunger can be seen which vertically extends in FIG. 3. Along the axis 11, the rod 2 is equipped with longitudinal struts 26 and perpendicular thereto with transversal struts 25.

The arrangement of longitudinal and transversal struts 25, 26 provides for an appropriate strength or robustness as well as to ensure proper molding in manufacture. The rod 2 is made of an ABS which is a comparably rigid plastic material. The stopper 3 is made of a TPE which is a comparably soft and elastic plastic material.

Figure 4:
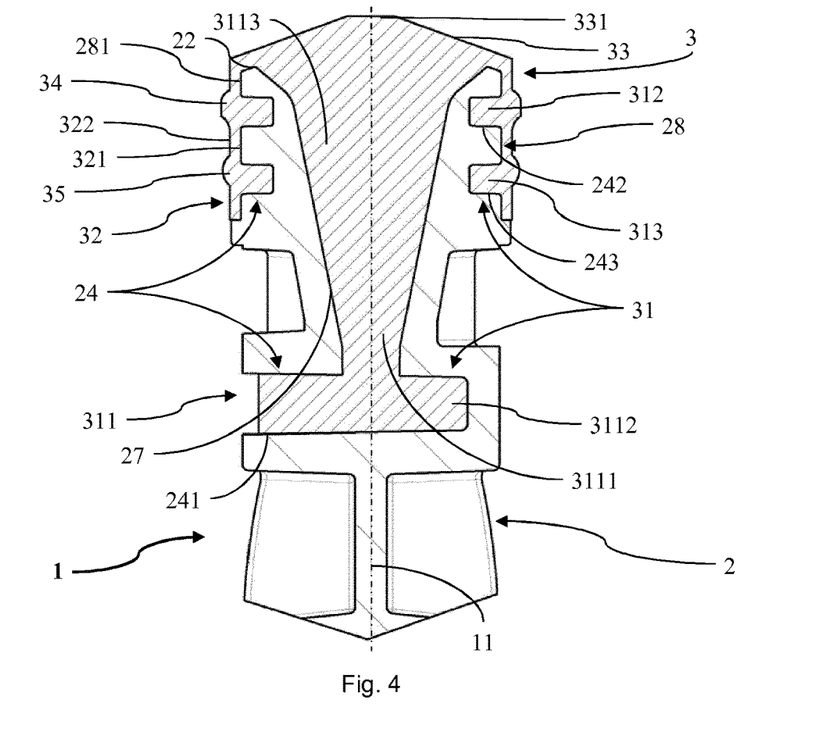
FIG. 4 shows the detail A of FIG. 3.

In FIG. 4 a section of the plunger 1 where the stopper 3 is mounted to the rod 2 is shown in more detail. The stopper 3 comprises a ring portion 32 or collar and the rod 2 has a cylindrical ring receiving section 28 near its distal end side 22 corresponding to the ring portion 32. The ring portion 32 has an inner stopper surface 321 and an outer stopper surface 322. The ring receiving section 28 has an outer rod surface 281 which lies adjacent to the inner stopper surface 321. Centrally, a recess 27 is formed in the rod 2 which downwardly tapers from its open top end at the distal end side 22 of the rod 2.

The rod 2 is equipped with a cavity structure 24 as first form fit structure having two arm sockets 241, a first circumferential groove 242 and a second circumferential groove 243. The first and second grooves 242, 243 radially extend into the outer radial rod surface 281 about the ring receiving section 28. They are axially spaced from each other such that the first groove 242 is closer to the distal end side 22 than the second groove 243. The arm sockets 241 are below the second groove 243 and radially extend from the axis 11 in one line to each other, i.e. from the axis 11 to the left and to the right. The left hand arm socket 241 is laterally open and the right hand arm socket 241 is laterally closed.

The stopper 3 is equipped with a projection structure 31 as second form fit structure which comprises an anchor portion 311, a first circumferential protrusion 312 and a second circumferential protrusion 313. The anchor portion 311 has a vertical shaft section 3111 ending in the distal end side 33 and two arm sections 3112. Each one of the arm sections 3112 radially projects from the shaft section 3111 to the left and to the right, respectively, into one of the arm sockets 241. The shaft section 3111 of the anchor portion 311 has a plurality of wall sections 3113 as stabilization elements arranged about the axis 11 and downwardly tapering along the axis 11.

The first and second circumferential protrusions 312, 313 of the projection structure 31 of the stopper 3 radially extend from the inner radial stopper surface 321 of the ring portion 32 towards the axis 11. They are axially spaced from each other such that the first circumferential protrusion 312 is closer to the axial end side 33 of the stopper 3 than the second circumferential protrusion 313. The first circumferential protrusion 312 of the projection structure 31 is arranged inside the first circumferential groove 242 of the cavity structure 24 and the second circumferential protrusion 313 is arranged inside the second circumferential groove 243.

Thus, the stopper 3 is locked to the rod 2 by the cavity structure 24 of the rod 2 and the projection structure 31 of the stopper 3 inter-engaging. In particular, a form fit or tight fit connection is provided by the stopper's 3 first projection 312, second projection 313 and arm sections 3112 being arranged in the rod's 2 first groove 242, second groove 243 and arm sockets 241, respectively. Like this, the stopper 3 is firmly secured on the rod 3 and additionally, supported by the wall sections 3112, deformation of the stopper 3 on the rod 2 due to friction forces acting on the stopper 3 when being translated and rotated in a chamber of a medical delivery device the plunger 1 is minimized.

The ring portion 32 of the stopper 3 further is equipped with a first circumferential bulge 34 and a second circumferential bulge 35. They both radially extend from the outer radial stopper surface 322 and, extend normal to the axis 11. The first circumferential bulge 34 is radially aligned relative to the first circumferential protrusion 312 and the second circumferential bulge 35 is radially aligned relative to the second circumferential protrusion 313. Like this, in the area of the bulges 34, 35 comparably lots of stopper material is provided allowing for a comparably good flexibility or compressibility of the stopper 3 where it contacts the chamber of the medical delivery device the plunger 1 is used. Thereby, a comparably high tightness can be achieved and it can be prevented that the stopper 3 is misaligned or tilted.

Figure 5:
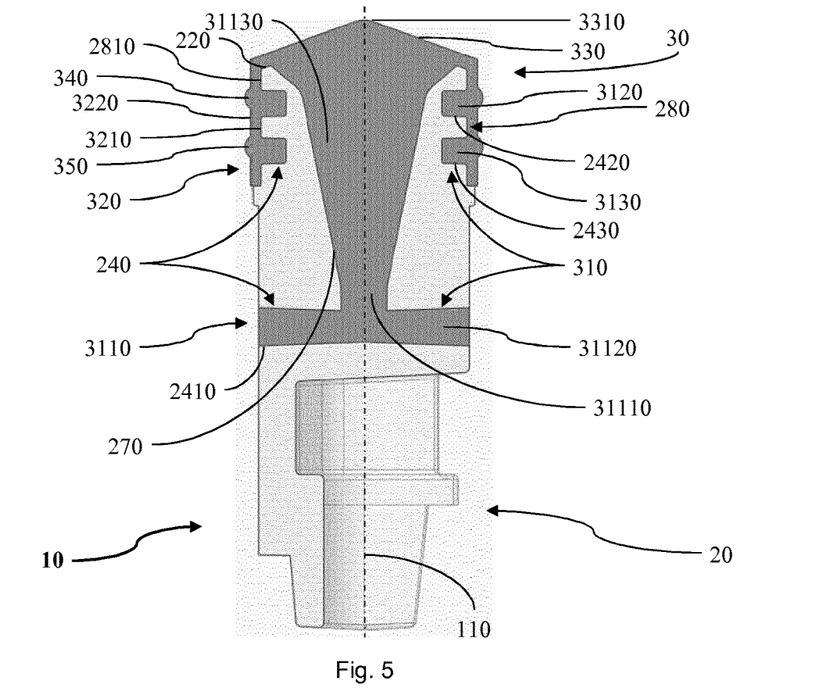
FIG. 5 shows a cross-sectional view of a detail of a second embodiment of a plunger according to the invention.
Figure 6:
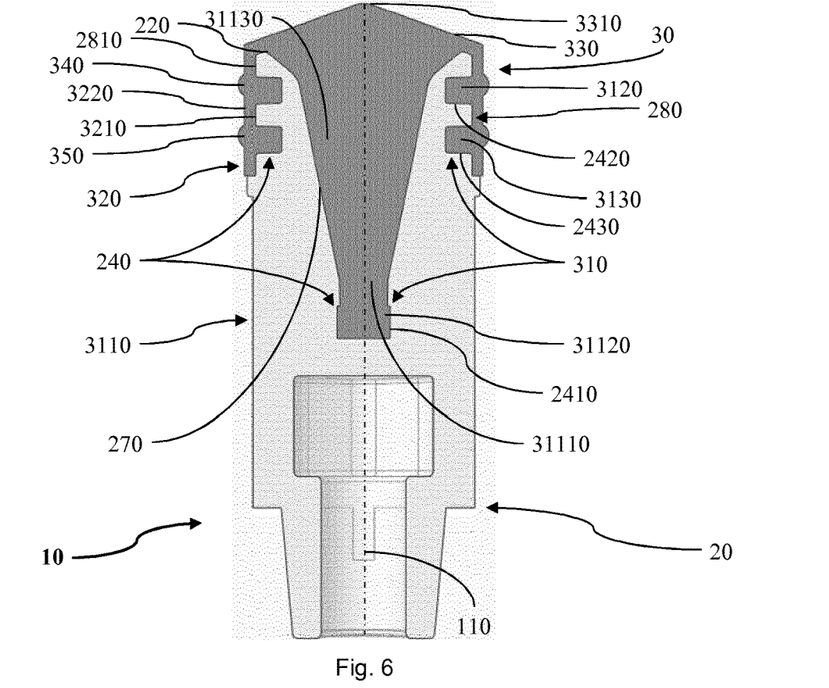
FIG. 6 shows a cross-sectional view of the detail of FIG. 5 turned by 90°.

FIGS. 5 and 6 show cross sectional views of a section of a second embodiment of a plunger 10 with an axis 110 according to the invention. Thereby, the plunger 10 is very similar to the plunger 1 shown in FIGS. 1 to 4. In particular, the plunger 10 comprises a rod 20 as rod element with: a cylindrical ring receiving section 280 near its distal end side 220 having an outer rod surface 2810; a central recess 270 downwardly tapering from its open top end; and a cavity structure 240 as first form fit structure having two arm sockets 2410, a first circumferential groove 2420 and a second circumferential groove 2430. The plunger 10 further comprises a stopper 30 with: a ring portion 320 having an inner stopper surface 3210 and an outer stopper surface 3220; a projection structure 310 as second form fit structure having an anchor portion 3110 with a vertical shaft section 31110 and two horizontal arm sections 31120, a first circumferential protrusion 3120 and a second circumferential protrusion 3130; a plurality of wall sections 31130 as stabilization elements; a first circumferential bulge 340; a second circumferential bulge 35; and an end side portion 330 with a tip 3310.

Whereas most of the features of the plunger 10 are for the same purpose and function in the same way as the respective features of the plunger 1, the following features are different:

Both arm sockets 2410 of the cavity structure 240 of the rod 20 are laterally open. They do taper from their open lateral ends towards the axis 110. Correspondingly, the arm sections 31120 of the anchor portion 3110 of the projection structure 310 of the stopper 30 do radially taper towards the axis 110 and do radially extend to the open end of the respective arm sockets 2410. Like this, the stopper 30 can additionally be laterally held and secured.

At its lower end, the rod 30 is equipped with a female connector structure for being coupled to an other element of a medical delivery device the plunger 10 is used with.

Both embodiment of plungers 1, 10 can advantageously be manufactured by an embodiment of the method according to the invention. Thereby, the rod 2, 20 of the plunger 1, 10 is obtained, e.g., in an injection moulding process. Then, the stopper 3, 30 of the plunger 1, 10 is moulded over the distal end 22, 220 of the rod 2, 20 such that the stopper 3, 30 is equipped with the projection structure 31, 310 and that the stopper 3, 30 is locked to the rod element 2, 20 by the projection structure 31, 310 of the stopper 3, 30 and the cavity structure 24, 240 of the rod 2, 20 inter-engaging.

This description and the accompanying drawings that illustrate aspects and embodiments of the present invention should not be taken as limiting the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A plunger for a medical delivery device comprising:
a rod element having a central axis, a distal end and a proximal end; and
a stopper mounted to the distal end of the rod element, wherein
the rod element has a first form fit structure and the stopper has a second form fit structure,
the stopper is locked to the rod element by the first form fit structure of the rod element engaging with the second form fit structure of the stopper,
the second form fit structure of the stopper has an anchor portion with a shaft section that essentially axially extends relative to the central axis of the rod element and an arm section located at a proximal end of the shaft section that essentially radially extends relative to the central axis of the rod element, the first form fit structure of the rod element has an arm socket that essentially radially extends relative to the central axis of the rod element and that is shaped to correspondingly receive the arm section of the anchor portion of the second form fit structure, and the stopper cannot be removed from the rod element without impairing or destroying the plunger when the arm section of the anchor portion of the second form fit structure of the stopper is arranged inside the arm socket of the first form fit structure.

2. The plunger of claim 1, wherein the rod element is made of a rod material and the stopper is made of a stopper material, the rod material being more rigid and less elastic than the stopper material.

3. The plunger of claim 1, wherein the shaft section of the anchor portion of the second form fit structure of the stopper essentially axially extends along the central axis of the rod element.

4. The plunger of claim 1, wherein the shaft section of the anchor portion of the second form fit structure of the stopper comprises at least one lateral stabilization element configured to prevent deformation of the shaft section of the anchor portion of the second form fit structure of the stopper.

5. The plunger of claim 4, wherein the lateral stabilization element of the shaft section of the anchor portion of the second form fit structure of the stopper comprises a wall section tapering along an axial direction towards a proximal end of the stopper.

6. The plunger of claim 1, wherein the rod element comprises a tapered recess, and the shaft section of the anchor portion has a wall section with a corresponding taper along an axial direction towards a proximal end of the stopper such that the tapered wall section of the stopper is arranged in the tapered recess of the rod element.

7. The plunger of claim 1, wherein the stopper comprises a ring portion defining an inner radial stopper surface and an outer radial stopper surface, the rod element has a ring receiving section with an outer radial rod surface essentially corresponding to the inner radial stopper surface of the stopper, the second form fit structure of the stopper has a circumferential protrusion essentially radially extending from the inner radial stopper surface of the ring portion of the stopper, the first form fit structure of the rod element has a circumferential groove essentially radially extending into the outer radial rod surface of the ring receiving section of the rod element, and the circumferential protrusion of the second form fit structure of the stopper is arranged in the circumferential groove of the first form fit structure of the rod element.

8. The plunger of claim 7, wherein the ring portion of the stopper is equipped with a circumferential bulge essentially radially extending from the outer radial stopper surface and essentially radially aligned relative to the circumferential protrusion of the second form fit structure of the stopper.

9. The plunger of claim 7, wherein the second form fit structure of the stopper has a second circumferential protrusion essentially radially extending from the inner radial stopper surface of the ring portion of the stopper, the first form fit structure of the rod element has a second circumferential groove essentially radially extending into the outer radial rod surface of the ring receiving section of the rod element, and the second circumferential protrusion of the second form fit structure of the stopper is arranged in the second circumferential groove of the first form fit structure of the rod element.

10. The plunger of claim 9, wherein the ring portion of the stopper is equipped with a second circumferential bulge essentially radially extending from the outer radial stopper surface and essentially radially aligned relative to the second circumferential protrusion of the second form fit structure of the stopper.

11. The plunger of claim 1, wherein the stopper has a conical distal end portion.

12. The plunger of claim 1, wherein the arm section of the anchor portion of the second form fit structure of the stopper includes
a first arm section that essentially radially extends relative to the central axis of the rod element in a first direction, and
a second arm section that essentially radially extends relative to the central axis of the rod element in a second direction that is opposite of the first direction; and wherein the arm socket of the first form fit structure of the rod element includes
a first arm socket that essentially radially extends relative to the central axis of the rod element in the first direction and that is shaped to correspondingly receive the first arm section of the anchor portion of the second form fit structure, and
a second arm socket that essentially radially extends relative to the central axis of the rod element in the second direction and that is shaped to correspondingly receive the second arm section of the anchor portion of the second form fit structure.

13. A medical delivery device, comprising:
a dosage chamber;
a liquid drug substance arranged in the dosage chamber;
an orifice coupled to the dosage chamber for providing the drug substance out of the device; and
a plunger according to claim 1, the plunger closing the dosage chamber.

14. A method of manufacturing a plunger according to claim 1, comprising:
obtaining a rod element of the plunger having a distal end, a proximal end and a first form fit structure; and
molding a stopper of the plunger over the distal end of the rod element such that the stopper is equipped with a second form fit structure and that the stopper is locked to the rod element by the second form fit structure of the stopper engaging with the first form fit structure of the rod element.

* * * * *